(12) United States Patent
Hanada et al.

(10) Patent No.: US 6,786,984 B1
(45) Date of Patent: Sep. 7, 2004

(54) TERNARY ALLOY AND APPARATUS THEREOF

(75) Inventors: Shuji Hanada, Miyagi (JP); Sadao Watanabe, Miyagi (JP); Naoya Masahashi, Miyagi (JP); Hideki Hosoda, Ibaraki (JP); Kikuo Nishi, Fukushima (JP)

(73) Assignee: Tomy Incorporated, Fukushima (JP)

( * ) Notice: Subject to any disclaimer, the term of this patent is extended or adjusted under 35 U.S.C. 154(b) by 0 days.

(21) Appl. No.: 09/710,430

(22) Filed: Nov. 9, 2000

(30) Foreign Application Priority Data

May 18, 2000 (JP) ........................................ 2000-146686

(51) Int. Cl.[7] ........................... C22C 14/00; C25C 16/00
(52) U.S. Cl. ......................... 148/421; 420/417; 420/422
(58) Field of Search ................................ 420/417, 422; 600/435; 433/21, 207; 602/19; 623/1.18, 16.11, 18.11; 606/62; 148/421

(56) References Cited

U.S. PATENT DOCUMENTS

| | | | | |
|---|---|---|---|---|
| 4,503,569 A | * | 3/1985 | Dotter | ........................ 623/1.19 |
| 4,795,458 A | * | 1/1989 | Regan | |
| 4,857,269 A | * | 8/1989 | Wang et al. | |
| 5,215,105 A | * | 6/1993 | Kizelshteyn et al. | |
| 5,429,501 A | * | 7/1995 | Farzin-Nia et al. | |
| 5,551,871 A | * | 9/1996 | Besselink et al. | |
| 5,827,231 A | * | 10/1998 | Harada | |
| 6,127,597 A | * | 10/2000 | Beyar et al. | |

FOREIGN PATENT DOCUMENTS

| | | | | |
|---|---|---|---|---|
| JP | 58-157934 A | * | 9/1983 | |
| JP | 10-219375 A | * | 8/1998 | |
| JP | 11-269585 A | * | 10/1999 | ........... C22C/14/00 |

OTHER PUBLICATIONS

"Shape Memory Alloys", Hodgon et al, from ASM Handbook vol. 2, Properties and Selection: Nonferrous Alloys and Special–Purpose Materials, 1992, pub. by ASM International, pp. 897–902.*

Nishiyama, Zenji et al., Martensitic Transformation, Academic Press, 1978, p. 231.

Baker, C., The Shape–Memory Effect in a Titanium–35 wt.–% Niobium Alloy, Metal Science Journal, 1971, vol. 5, pp. 92–100.

Ahmed, T. et al., Martensitic Transformation in Ti–(16–26 at %) Niobium Alloy, Journal of Materials Science 31, 1996, pp. 4267–4276.

R. Boyer, G. Welsch and E. W. Collings, *Materials Properties Handbook: Titanium Alloys*, First Printing: Jun. 1994; ASM International, The Materials Information Society, 9 pages.

Kenneth J. Anusavice, D.M.D., Ph.D, *Phillips' Science of Dental Materials*, Tenth Edition, Chapter 28, Wrought Base Metal and Gold Alloys, 1996, pp 631 and 648–651, W.B. Saunders Company.

* cited by examiner

*Primary Examiner*—Roy King
*Assistant Examiner*—Harry D. Wilkins, III
(74) *Attorney, Agent, or Firm*—Kenyon & Kenyon (57) ABSTRACT

This present invention relates to an alloy comprising Sn, at least one of Ti and Zr and at least one of Nb and Ta as the major elements. The total percentage of the Nb and Ta in the alloy material is preferably from 8 to 20 atom % and the percentage of the Sn in the alloy material is preferably from 2 to 6 atom %. The alloy material is preferably Ni-free and has shape memory characteristics or superelasticity.

23 Claims, 10 Drawing Sheets

| Sample | Ti (at.%) | Nb (at.%) | Sn (at.%) |
|---|---|---|---|
| 10Nb4Sn | 86 | 10 | 4 |
| 10Nb5Sn | 85 | 10 | 5 |
| 10Nb6Sn | 84 | 10 | 6 |
| 12Nb3Sn | 85 | 12 | 3 |
| 12Nb4Sn | 84 | 12 | 4 |
| 12Nb5Sn | 83 | 12 | 5 |
| 12Nb6Sn | 82 | 12 | 6 |
| 12Nb7Sn | 81 | 12 | 7 |
| 12Nb8Sn | 80 | 12 | 8 |
| 14Nb3Sn | 83 | 14 | 3 |
| 14Nb4Sn | 82 | 14 | 4 |
| 14Nb5Sn | 81 | 14 | 5 |
| 14Nb6Sn | 80 | 14 | 6 |
| 14.5Nb3Sn | 82.5 | 14.5 | 3 |
| 14.5Nb4Sn | 81.5 | 14.5 | 4 |
| 14.5Nb5Sn | 80.5 | 14.5 | 5 |
| 15Nb3Sn | 82 | 15 | 3 |
| 15Nb4Sn | 81 | 15 | 4 |
| 15Nb5Sn | 80 | 15 | 5 |
| 15.5Nb3Sn | 81.5 | 15.5 | 3 |
| 15.5Nb4Sn | 80.5 | 15.5 | 4 |
| 15.5Nb5Sn | 79.5 | 15.5 | 5 |
| 16Nb4Sn | 80 | 16 | 4 |
| 16Nb5Sn | 79 | 16 | 5 |
| 16Nb6Sn | 78 | 16 | 6 |
| 17Nb4Sn | 79 | 17 | 4 |
| 17.5Nb4Sn | 78.5 | 17.5 | 4 |
| 18Nb4Sn | 78 | 18 | 4 |
| 18Nb5Sn | 77 | 18 | 5 |
| 18Nb6Sn | 76 | 18 | 6 |
| 18.5Nb4Sn | 77.5 | 18.5 | 4 |
| 19Nb4Sn | 77 | 19 | 4 |
| 20Nb4Sn | 76 | 20 | 4 |
| 20Nb6Sn | 74 | 20 | 6 |

Before heating        After heating

Before heating   After heating

Simplified bend test results

Before heating     After heating

● : Recovery from deformation at room temperature

▲ : Recovery from deformation in liquid nitrogen

× : No recovery

TERNARY ALLOY AND APPARATUS THEREOF

FIELD OF THE INVENTION

This invention relates to shape memory alloys which are transiently or semipermanently usable in almost every part of human.

BACKGROUND OF THE INVENTION

The Ti (titanium)/Ni (nickel) alloy (Nitinol) has been transiently or semipermanently employed in almost every part of human as a shape memory alloy or a superelastic alloy for biological use. In recent years, however, there arises a problem of a human Ni allergy, especially in European countries. Use of the Ti/Ni alloy would be prohibited before long from the viewpoint of biocompatibility. Accordingly, it has been required to provide a shape memory alloy free from elements which are toxic or allergic to human.

Figure 1:
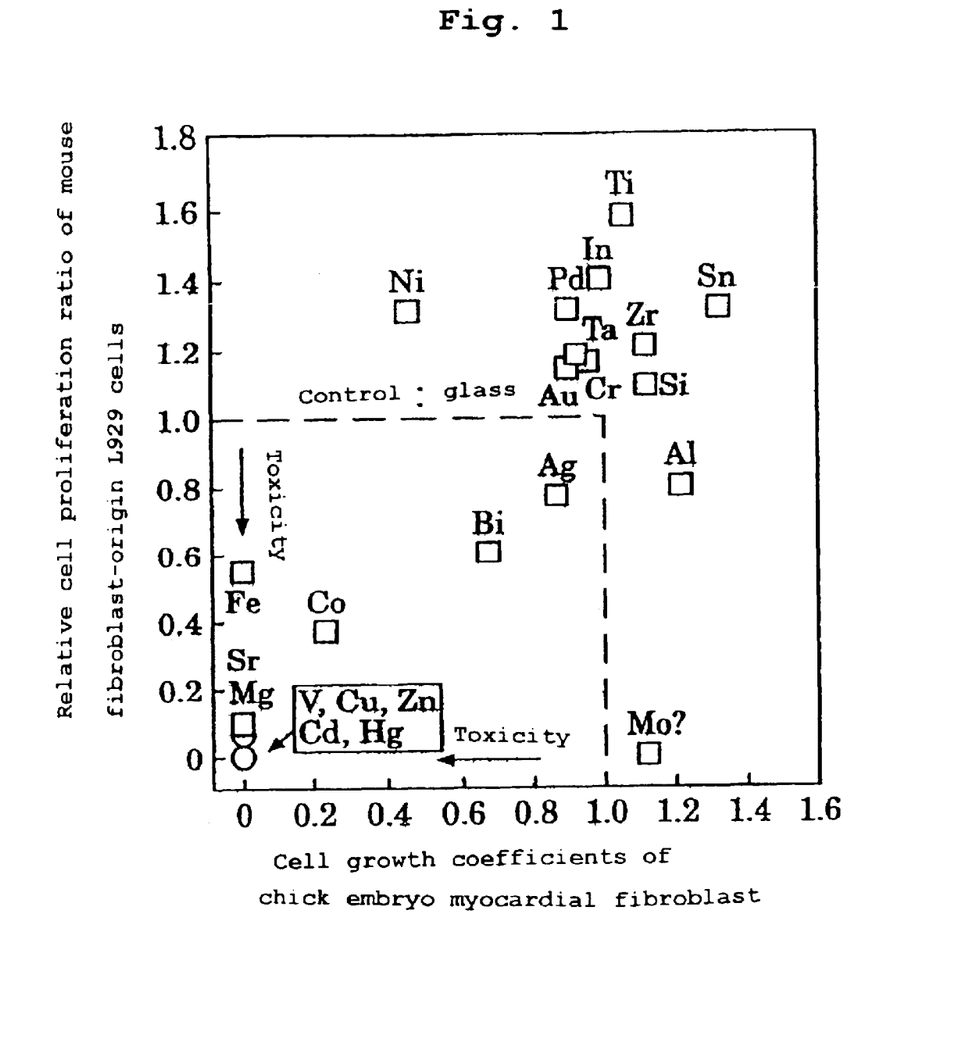
FIG. 1 is a graph showing cytotoxicity of pure metals.
Figure 2:
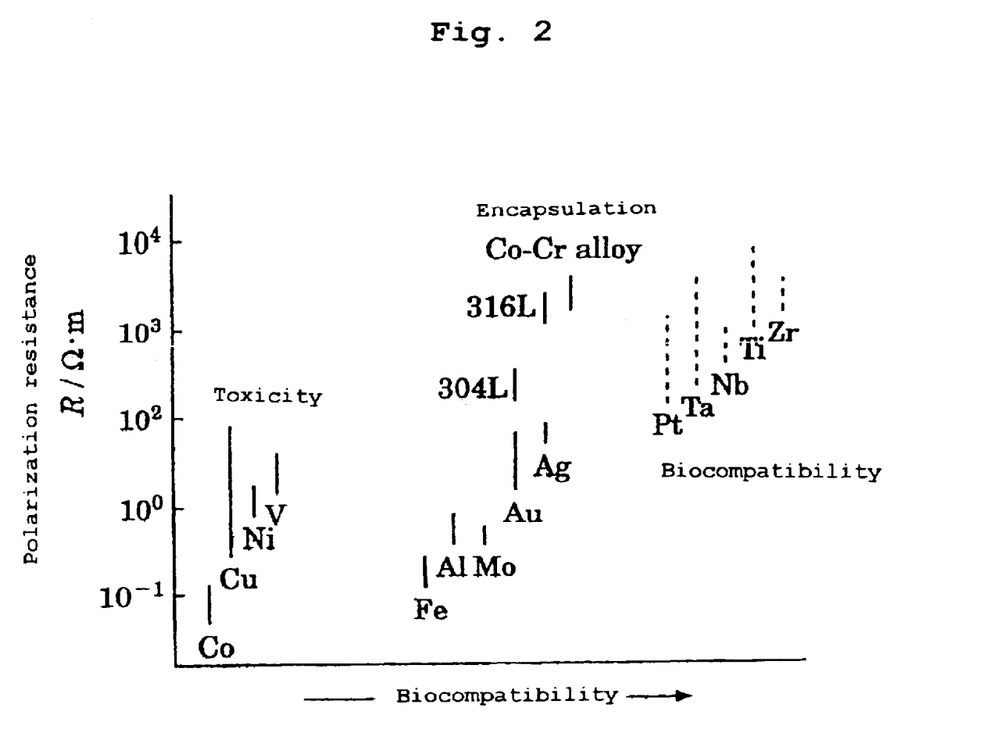
FIG. 2 is a graph showing relationship between polarization resistance and biocompatibility of pure metals, a Co—Cr alloy and stainless steel.

FIG. 1 summarizes the cell growth coefficients of chick embryo myocardial fibroblast and relative cell proliferation ratios of mouse fibroblast-origin L929 cells concerning various pure metals. These data indicate that V, Cd, Co, Cu, Zn, Hg, Al, Cr, etc. have strong cytotoxicity, while Zr, Ti, Nb, Ta, Pt, Au, etc. are excellent in biocompatibility. FIG. 2 shows a relationship between polarization resistance, which serves as an indication of corrosion resistance in vivo, and biocompatibility. As FIG. 2 shows, Pt, Ta, Nb, Ti and Zr are excellent in biocompatibility.

As discussed above, the Ti/Ni alloy has been almost exclusively employed as a shape memory alloy for biological use. As there arises a fear for the serious allergy to Ni, Ni-free shape memory alloys have attracted public attention. On the other hand, Baker and Ahmend et al. reported Ti alloys, but the Ti alloys reported by them are not satisfactory as a shape-memory alloys for biological use.

SUMMARY OF THE INVENTION

Under these circumstances, the inventors have made extensive studies to provide Ti alloys having highly biocompatible elements and preferably having the shape memory effects for biological use, and found that a ternary alloy containing Sn as the third element can be a non-toxic and non-allergic alloy having an appropriate shape memory property for biological use. The present invention was accomplished based on this finding.

The alloy according to the present invention is an alloy material comprising (1) Sn (tin), (2) at least one of Ti (titanium) and Zr (zirconium), (3) and at least one of Nb (niobium) and Ta (tantalum).

The present invention also provides a orthodontic appliances, an artificial dental implant, an artificial arthrosis, a born material, a born fixator, a thrombus inhibitor, a catheter introducer, and a Harrington bar comprising the said alloy.

DETAILED DESCRIPTION OF THE INVENTION

The alloy according to the present invention is an alloy material comprising (1) Sn (tin), (2) at least one of Ti (titanium) and Zr (zirconium), (3) and at least one of Nb (niobium) and Ta (tantalum). The combination of Ti, Nb and Sn is preferable as a combination of ternary major constituents.

The alloy of the present invention can include other elements (preferably biologically compatible elements, e.g., Zr, Ti, Nb, Ta, Pt and Au). The amount of other elements are preferably up to 5 atom % based on total % of the ternary major constituent (the sum of the ternary major constituent is 100 atom %). It is preferable that the alloy of the present invention does not include cytotoxic elements (e.g., V, Cd, Co, Cu, Zn, Hg, Al and Cr).

In the alloy according to the present invention, the total percentage of Ti and Zr is preferably from 90 to 74 atom %, the total percentage of Nb and Ta is preferably from 8 to 20 atom % and the percentage of Sn is preferably from 2 to 6 atom %. The total percentage of the Ti and Zr is more preferably from 87 to 79 atom %, the total percentage of Nb and Ta is more preferably from 10 to 16 atom % and the percentage of Sn is more preferably from 3 to 5 atom %.

The alloy of the present invention preferably has shape memory characteristics or superelasticity, preferably at the human body temperature.

The alloy of the present invention can be obtained by well known methods, for example, as described below.

The alloy of the present invention can be used to various manufactures, and preferably to manufacture variety medical instruments and the like, as described below.

These manufactures can be produced by the ordinary methods as described below.

The alloy of the invention can be produced similarly to those for known alloy materials, i.e., by mixing starting materials at a definite ratio and melting. The melting method is not restricted, for example, the present alloy can be produced by using the arc melting process or the high-frequency melting process. Since the alloy of the invention is composed of active metals, it is favorable that the melting is carried out in vacuo or in an inert gas atmosphere. It is possible to obtain an alloy mass from the starting metals in the molten state. Alternatively, an alloy powder can be obtained by, for example, the atomization process (gas-spraying process). An example of the atomization process will be illustrated in below. The atomization process is the most widely employed process at present. Use may be made of, for example, an apparatus manufactured by Crucible Co. In this process, a starting material or a cast mass is molten under high frequency induction in high vacuo and then once received in a tundish. Next, the molten matter is passed through a nozzle to give a hot molten stream with a small diameter which is then atomized by collision with a high-pressure argon gas. The powder is collected with a collector located in the lower part of a spray chamber. The thus collected powder is maintained in an inert atmosphere and transported to the next step. Powdery metals are highly expected as useful since they can provide uniform microfibers with little segregation, though they contain a large amount of alloy elements. To prevent reactions with active metals, metal powders are usually produced in vacuo or under an inert atmosphere.

The alloy of according to the present invention can be used in the various apparatus. Several examples of the apparatus for which the alloy of the present invention can be used as a material will be illustrated below, but the use of the alloy of present invention is not restricted thereto.

The alloy according to the invention is useful particularly in the medical instruments as will be described below. In addition, it may be used as described in "Minimally Invasive Therapy & Allied Technologies Vol. 9 No. 2, ISIS Medical Media" (the text of which is incorporated herein by reference), and the like.

The alloy according to the invention can be used as a material of Harrington's bar. The stainless bar has been used as a Harrington's bar which is employed as a corrective orthosis for scoliosis. However, such a stainless bar shows a decrease in the corrective force applied on the spine with the passage of time. Therefore, it becomes necessary to perform the operation again to restore the corrective force, which inflicts a serious pain on a patient. When the alloy according to the invention is used as a Harrington's bar, the corrective force can be controlled merely by heating the corrective bar externally. Thus no operation is needed any more and the burden to the patient can be relieved.

The alloy according to the invention also can be used as a material of artificial joints. In our daily activities, a load 3 to 6 times, even 10 times in the largest case, more than the body weight is applied on joints. Loads are repeatedly applied on the hip joints $10^6$ times per year. Therefore, artificial joints to be used under these conditions should be made of materials which are excellent in mechanical properties such as abrasion resistance. The alloy according to the invention is also useful in artificial joints, since it is excellent in abrasion resistance and enables the formation of a self-locking joint system, wherein the material per se has a fixation function, owing to the shape memory effect and the superelasticity thereof.

The alloy according to the invention can be used as a material of bone fixation devices (bone plates, intramedullary pins, intramedullary nails, staples, wires, etc.). Conventional bone fixation devices to be used in orthopedics or treating fracture are mainly made of stainless steel or Co/Cr alloy. Use of the alloy according to the invention in these devices makes it possible to impart a fixation force recovering into the original shape due to the shape memory effect and to sustain a continuous and stable fastening force owing to the superelasticity.

The alloy according to the invention is also usable forming antithrombotic wires (stents, etc.). In the fields of artificial organs and treatments for circulatory diseases, a wire made of the alloy according to the invention can be attached to the ventricular wall as an artificial heart actuator.

The antithrombotic wires (stents, etc.) using the alloy of the invention which are to be inserted into the vessel to enlarge the vessel thereby preventing blood stagnation or thrombus formation caused by the vascular constriction and filters for trapping blood clots migrating in the vena cava. Thus, the risk of damaging vessels or nerves at the insertion of such a device can be relieved and an operation can be conveniently and quickly carried out.

The alloy according to the invention is also usable in catheter guides. To enlarge a stent in a heart vessel or to observe the inner face of a vessel, it is needed to insert a device such as catheter into the vessel. By employing the shape memory alloy of the invention as the guide wire to be used in the insertion of the catheter, the catheter can be safely and easily introduced.

Furthermore, the alloy according to the invention is usable in artificial tooth implants and orthodontic wires. There have been used orthodontic wires made of stainless steel or Co/Cr alloy. Although these conventional orthodontic wires can exert large corrective force upon a slight deformation owing to the high elastic modulus and a low elastic elongation, they suffer from a problem of being liable to undergo plastic deformation. By taking advantage of the superelastic function of the alloy according to the invention, in contrast thereto, no plastic deformation arises even upon a strain of 10%. In addition, the corrective force is scarcely increased due to the nonlinear characteristics of the modulus of elasticity caused by the stress-induced martensitic transformation. Owing to these characteristics, an orthodontic wire made of the alloy of the invention can be applied while sustaining an adequate corrective force even upon large deformation at the application, which not only facilitates the application but also contributes to the achievement of favorable therapeutic effects. Moreover, unpleasantness of a patient can be thus relieved.

The above-described medical devices can be formed by molding and processing the alloy according to the invention by known methods to give a desired shape and size. Also, these devices can be employed in practice by known methods described in, for example, "Using Nitinol Alloys, Darel E. Hodgson et al., Shape Memory Applications, Inc." (the text of which is incorporated herein by reference).

When the alloy of the invention is obtained as an ant alloy mass, the segregation of the material is eliminated by a casting process (the lost wax process, the precise casting process, etc.) or the hot casting/homogenization treatment. Then, it can be molded into a desired shape by various processes (rolling, rod drawing, cutting, etc.). For example, the alloy obtained by hot forging may be shaped into a rod with an appropriate diameter by hot rolling or hot swaging and then subjected to cold rod drawing and process annealing repeatedly to give a wire of a definite size. It is also possible to obtain a plate material by successively performing hot rolling and cold rolling. These materials (wires or plates) can be obtained almost in the same manner as in the spring processing of piano wires or stainless wires but the heating treatment. In the precise casting process, a mold material is filled into a resin model in a three-dimensional shape and then the resin is eliminated by heating the mold or solubilizing the resin in a solvent. Thus, the mold has a hollow in the same shape as the three-dimensional resin model. Then a molten metal is poured into this hollow in the mold and, after cooling, the mold is taken off. Investment casting process is one of the precise casting processes wherein a model is formed by wax, polystyrol resin, etc., coated with a fine fireproofing powder containing ethyl silicate or sodium silicate and dried. Next, a molten metal is poured into the mold which is then heated to a high temperature so that the wax or polystyrol resin is molten and flown out and the mold is baked. This process is employed in producing cast articles having a high accuracy and an excellent texture. Markast process, wherein frozen mercury is employed, falls within the category of this process. When the alloy of the invention is obtained as a powdery alloy, it can be molded by the sintering process, the powder metallurgy, etc. It is also possible to perform the molding in a single step by melting and sintering the powdery metal feedstock. In the step of molding the powder, it is also possible to employ injection molding so as to give a molded article in a complicated shape. The injection molding can be carried out by blending the powdery alloy with thermoplastics, injection-molding the feedstock thus formed, removing the thermoplastics by heating and then sintering the residue. The sintering process is a technique wherein powders are blended and mixed, and the obtained feedstock is molded usually with the use of a mold, etc. and then heated and solidified (sintering) to a temperature lower than the melting point of the main component to thereby give materials or parts. In the field of metallic materials, this technique is called powder metallurgy. General production process of sintering includes the following steps: preparation of powders, blending/mixing of powders, molding, sintering and post-treatment.

The term "room temperature" used herein is about 15 to 30° C., preferably 20 to 25° C.

The term "human body temperature" used herein is about 30 to 40° C., preferably 36 to 37° C.

EXAMPLE

An example of the present invention is given below by way of illustration by reference to the attached drawings and not by way of limitation.

Figure 3:
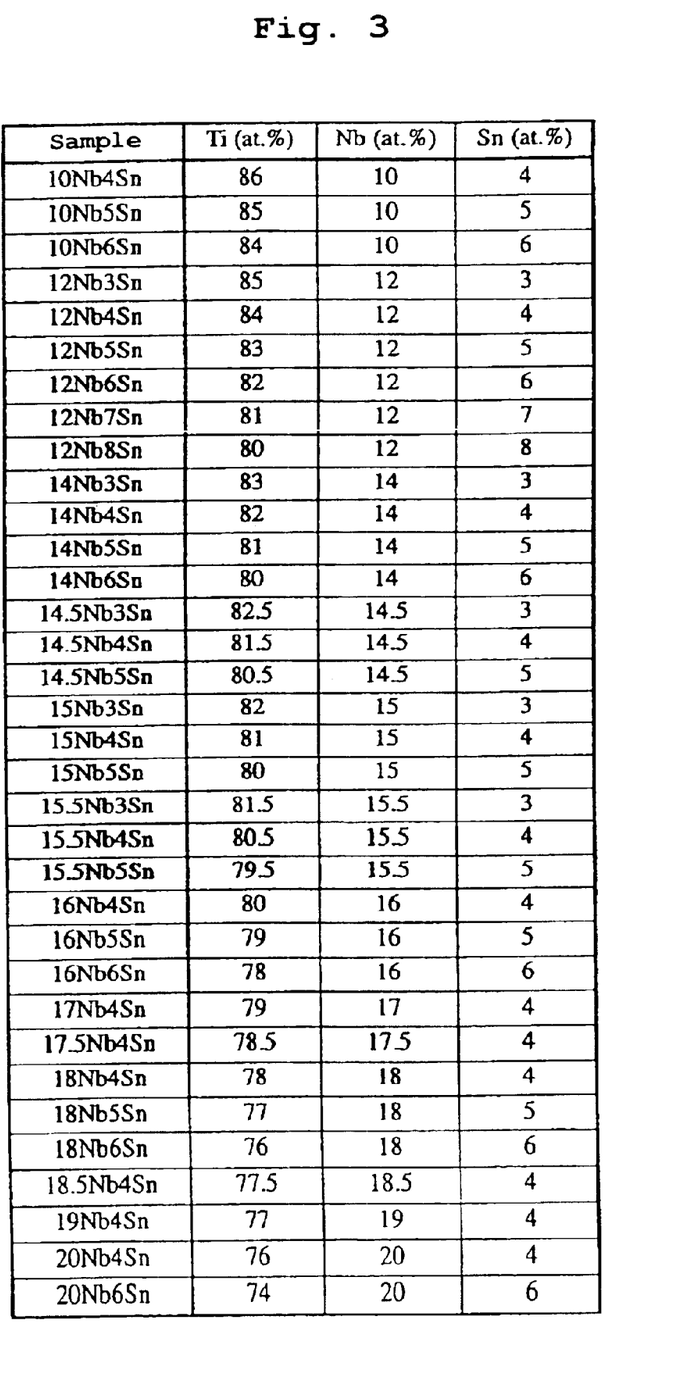
FIG. 3 provides a composition list of the alloys employed in the comparative experiment in the invention.

Alloy compositions of samples prepared in this experiment are listed in FIG. 3. To determine the experimental composition range, each composition was selected in such a manner that single β phase was obtained at the quenching step and the martensite transformation temperature was not elevated too high with reference to Murray's Ti-Nb binary system (J. L. Murray: Phase Diagram of Binary Titanium Alloys, ASM, Materials Park, Ohio, (1987), 188.) diagram and composition-dependency of Ti-Nb binary system martensite transformation temperature summarized by Ahmed et al. (T. Ahmed, H. J. Pack: J. Mat. Sci., 31 (1996), 4267.)

Starting with pure Ti (purity: 99.99%), pure Nb (purity: 99.99%) and pure Sn (purity: 99.99%), alloys were prepared by argon arc melting techniques.

Before weighing to give the desired composition, pure Ti and pure Nb were washed with a solution composed of 25% by volume of hydrofluoric acid, 25% by volume of nitric acid and 50% by volume of pure water and then washed with acetone, while pure Sn was washed with acetone to thereby cleanse the surface. Melting was carried out in an argon atmosphere in an arc melt oven with the use of a water-cooled copper hearth and a non-consumable tungsten electrode to give button-like ingots. Before melting, Ti getter was molten for 10 minutes so that residual contaminants such as oxygen were eliminated. Each ingot weighed about 30 g. To minimize the segregation of the alloy components, the ingots were located upside down and repeatedly molten and solidified 4 times.

The molten ingots were homogenized by heating to 1100° C. for 12 hours and then cooled in the oven. Next, the ingots were cold rolled to sheets of 1 mm in thickness. Specimens in various shapes were cut from the sheets with the use of an electric discharge machine and the oxide layer on the surface was removed by polishing. Subsequently, the specimens were vacuum-packed in an opaque quartz tube and, after sealing, subjected to solution heat treatment at 950° C. for 30 minutes, and then quenched in ice water.

Figure 4:
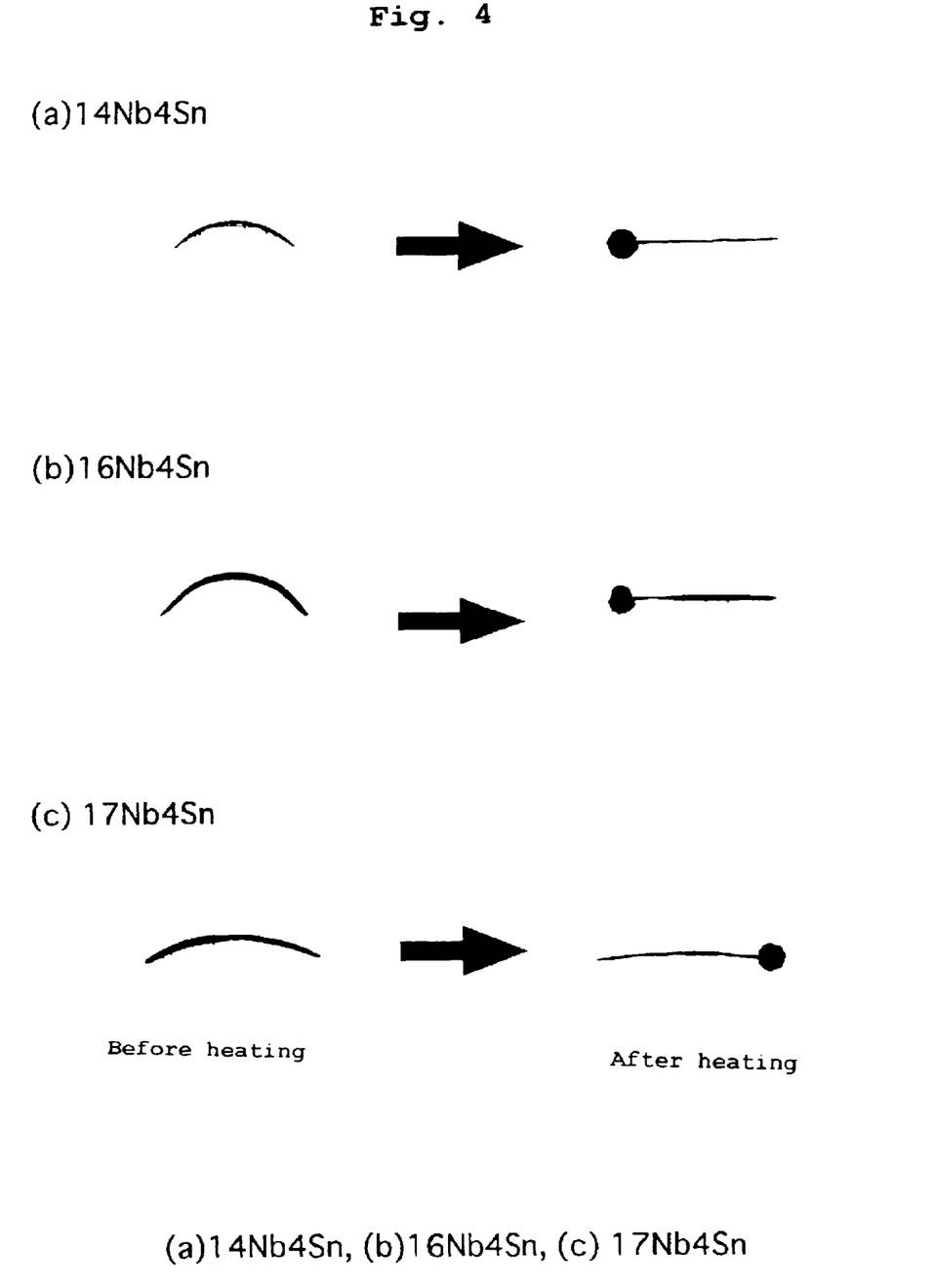
FIG. 4 provides photographs showing an example of the simplified bond test (before and after heating).
Figure 5:
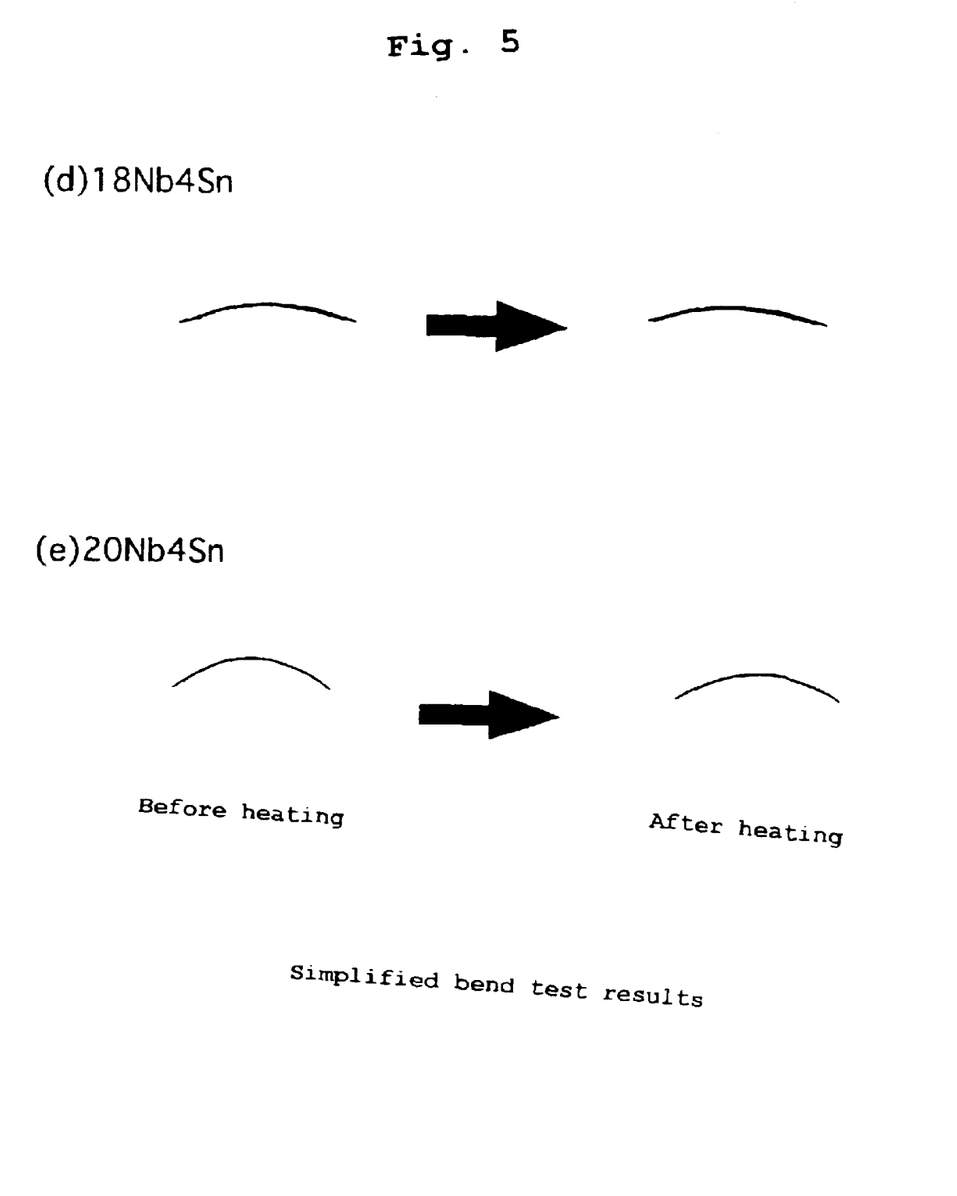
FIG. 5 provides photographs showing an example of the simplified bend test (before and after heating).
Figure 6:
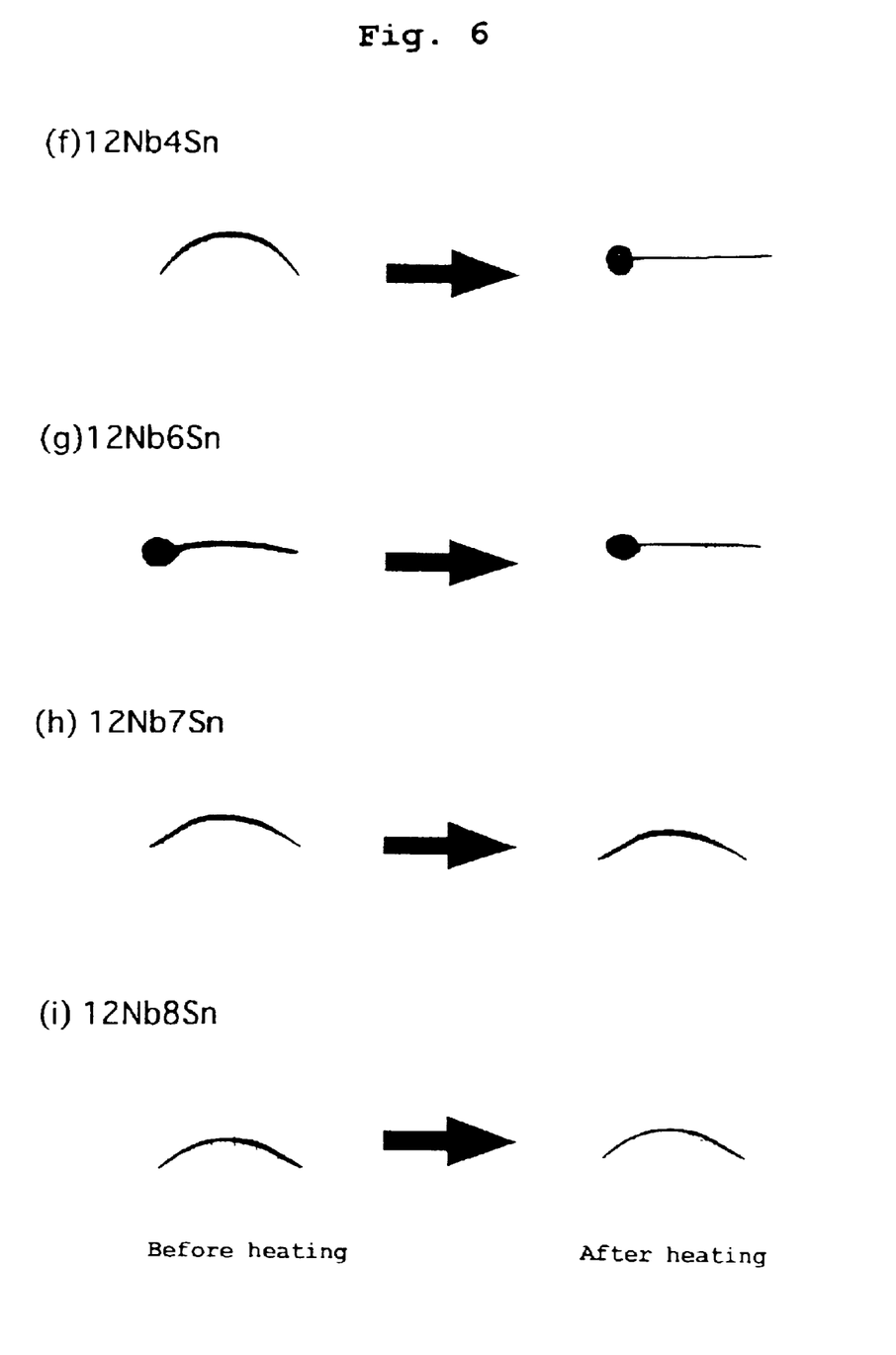
FIG. 6 provides photographs showing an example of the simplified bend test (before and after heating).

A simplified bend test was performed to examine whether the alloy thus produced had shape memory effect or not. FIGS. 4, 5 and 6 are photographs showing the test results wherein each photograph in the left side shows a specimen having been wound around a rod and, after causing transformation, taken off from the rod, while the right one shows the specimen after heating.

In FIGS. 4 and 5, a to e show the shape memory effects of alloys containing 4 atom % of Sn. These photographs are presented in increasing order of Nb content. The 14Nb4Sn, 16Nb4Sn and 17Nb4Sn specimens recovered their own shapes, while no recovery was observed in the 18Nb4Sn and 20Nb4Sn specimens. In these photographs, clay holds, which were employed to put up the specimens, are observed at the end of specimens having been completely recovered their original (i.e., linear) shapes. Regarding the degree of transformation of the specimens before heating, the 14Nb4Sn, 16Nb4Sn and 20Nb4Sn specimens showed considerably large deformation after taking off from the rods. Namely, these specimens showed large residual strains. In contrast, the 17Nb4Sn and 18Nb4Sn specimens showed less deformation, compared with the above three specimens, after taking off from the rods and relieving the transformation stress.

FIGS. 6 (f) to (i) show of alloys containing 12 atom % of Nb. These photographs are presented in increasing order of Sn content. The 12Nb4Sn' and 16Nb6Sn specimens recovered their own shapes, while no recovery was observed in the 12Nb7Sn and 12Nb8Sn specimens. The 12Nb6Sn specimen showed less residual strain than the other three specimens.

Figure 7:
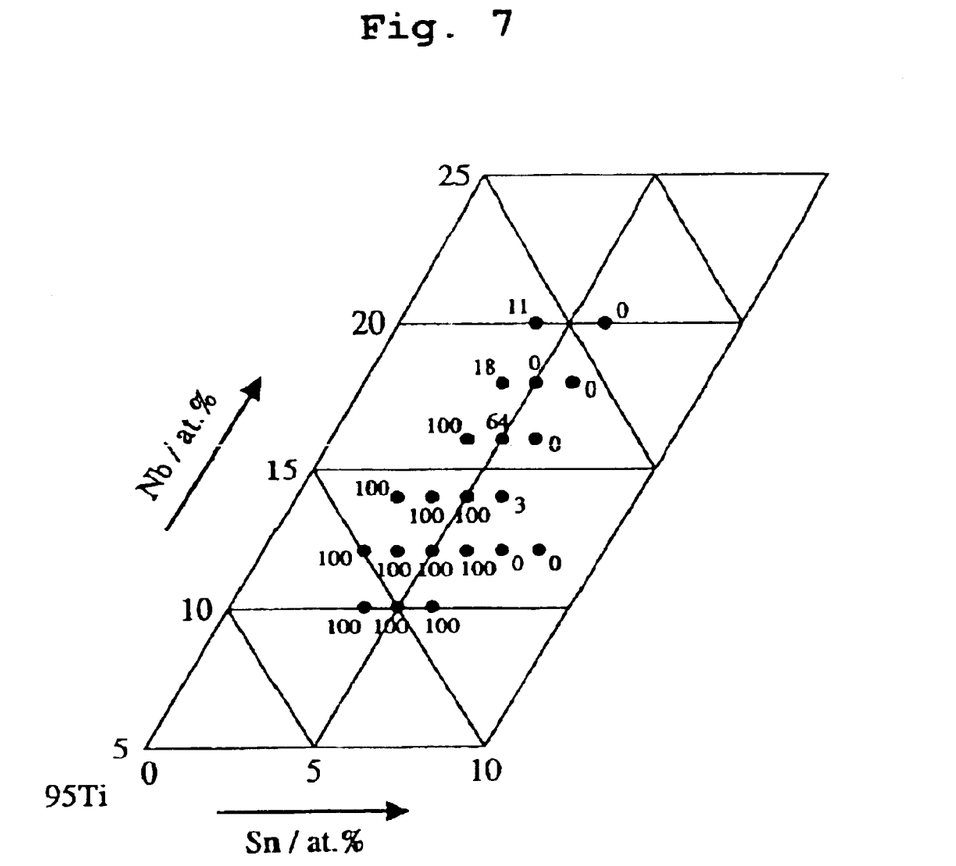
FIG. 7 is a graph showing the shape recovery ratio in the simplified bend test.

The bend test as described above was carried out and the bending ratios (beforehand after heating) of the specimens were calculated. FIG. 7 summarizes the results. As FIG. 7 shows, the specimens completely recovered their original shapes (recovery ratio: 100%) in the low Nb and low Sn side. In the 14Nb6Sn, 16Nb5Sn and 18Nb4Sn specimens, residual strain remained even after heating. In the specimens with more Nb or Sn contents, no shape memory effect was observed under the experimental conditions employed. Hereinafter, $M_s$ stands for martensite transformation starting temperature; $M_f$ stands for martensite transformation finishing temperature; $A_s$ stands for austenite transformation starting temperature; and $A_f$ stands for austenite transformation finishing temperature.

Figure 8:
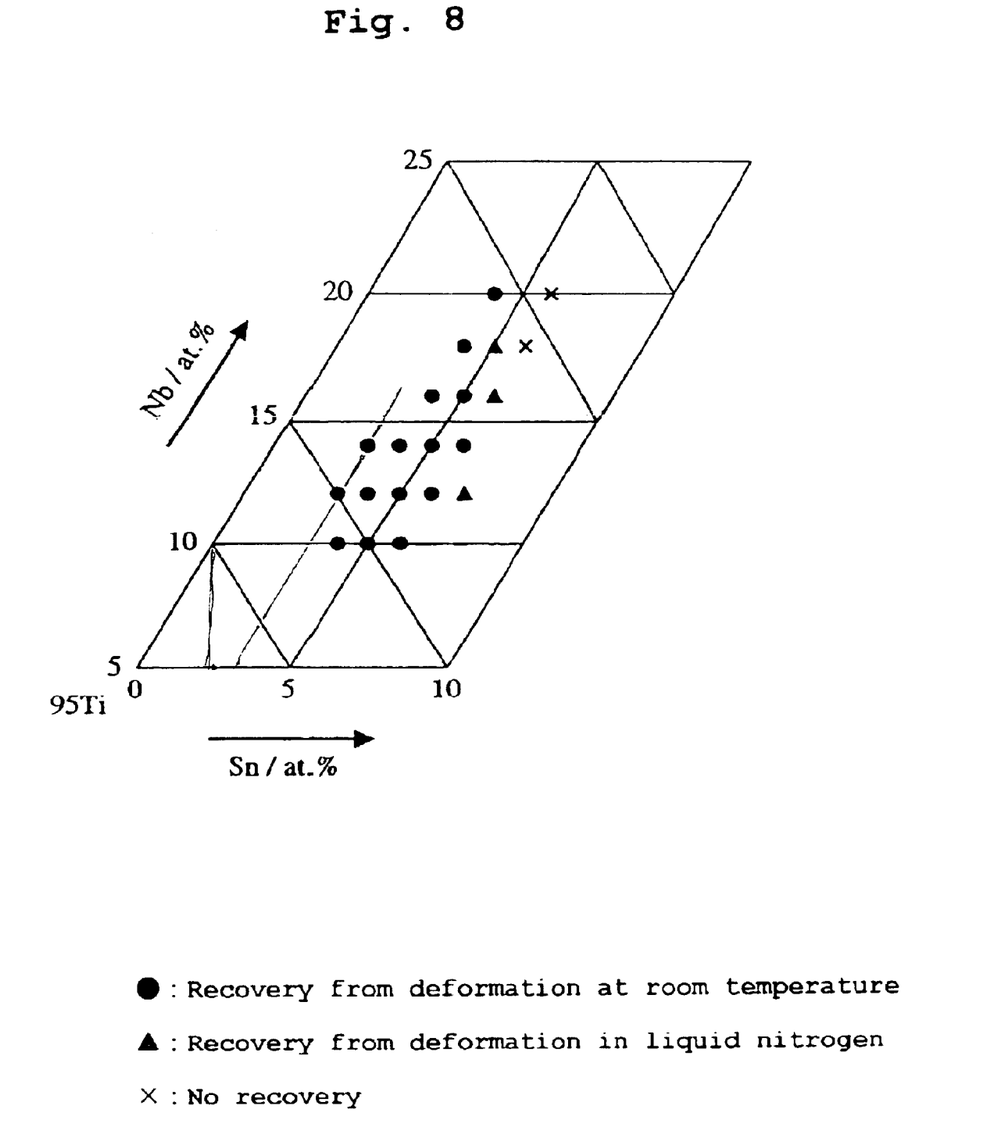
FIG. 8 is a graph showing the occurrence of the shape memory effect.

All of the procedures in the bend test described so far were performed at room temperature. Further, the specimens were deformed in liquid nitrogen and then heated so as to examine the occurrence of shape recovery. FIG. 8 summarizes the occurrence of the shape memory effect involving the cases tested in liquid nitrogen. A specimen showing shape recovery, even a little, upon heating was regarded as having the shape memory effect. As a result, the 12Nb7Sn, 16Nb6Sn and 19Nb5Sn specimens showed no shape recovery at room temperature but recovered their original shapes when deformed at the liquid nitrogen temperature. Among the alloy specimens prepared herein, 18Nb6Sn and 20Nb6Sn showed no shape memory effect both at room temperature and at the liquid nitrogen temperature.

Figure 9:
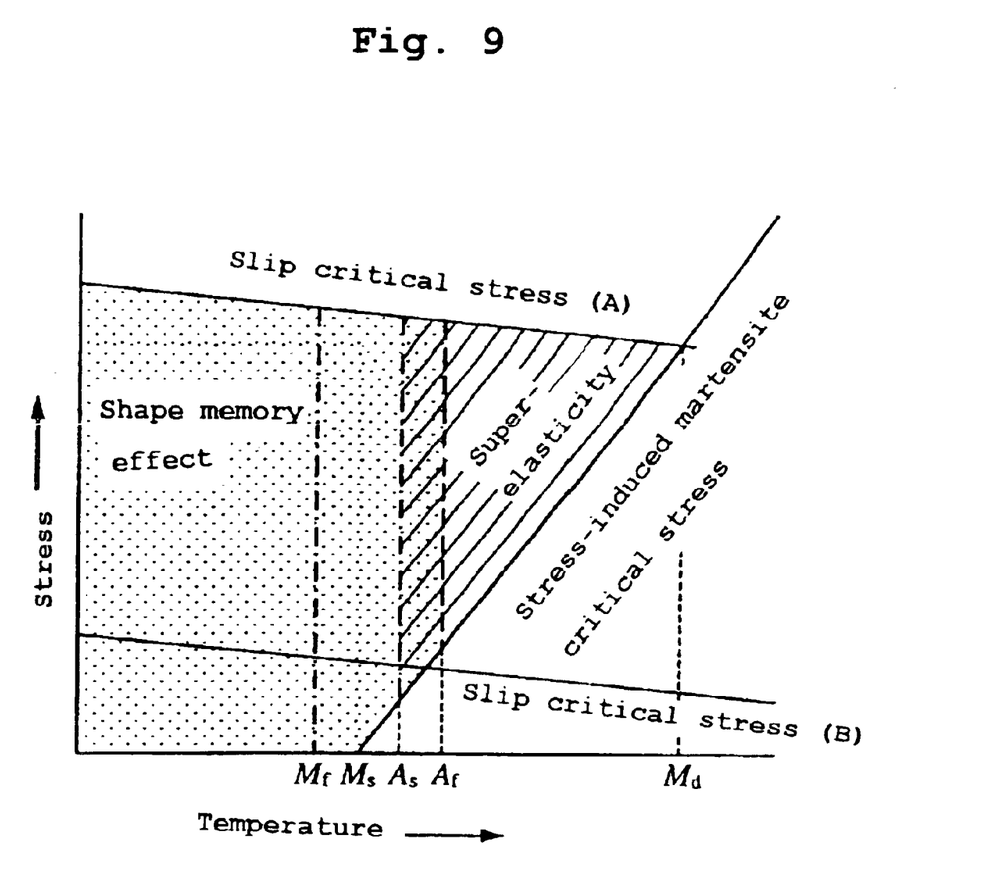
FIG. 9 is a model view showing conditions for the occurrence of the shape memory effect and superelasticity (pseudo-elasticity).

Now, the martensite transformation temperature and the occurrence of the shape memory effect will be briefly illustrated. FIG. 9 is a model view showing conditions for the occurrence of the shape memory effect and superelasticity (pseudo-elasticity). As FIG. 9 shows, it is needed for the occurrence of the shape memory effect that martensite transformation arises at the transformation temperature or stress-induced martensite is formed by loading a stress at the deformation and the martensite does not undergo complete reveres transformation but remains merely by unloading. The strain due to the martensitic twin crystal deformation is recovered by heating to $A_f$ or higher temperatures so as to induce reverse transformation.

The fact that no shape recovery was observed in the bend test at room temperature indicates that the corresponding alloy is not in the martensitic phase but remains as the matrix at room temperature, or stress-induced martensite, if formed, is completely reverse-transformed by unloading. In the latter case, complete superelasticity is observed. In the test as described herein, however, no complete superelasticity was obtained. Therefore, the alloys showing no shape recovery in the bend test at room temperature have $M_s$ lower than room temperature and not undergo stress-induced martensite transformation. As FIG. 8 shows, moreover, some of Nb rich and SN-rich specimens not showing shape recovery at room temperature recovered into the original shapes at the liquid nitrogen temperature. Based on these facts, it is found out that the martensite transformation temperature tends to be lowered with an increase in the Nb and Sn contents in the ternary Ti—Nb—Sn alloys.

As shown in the photographs of FIGS. 4, 5 and 6, the residual strain is decreased at certain alloy compositions. The reason for this phenomenon can be understood as follows concerning superelasticity. First, in case wherein $A_s$ of such an alloy is not higher than room temperature, its $A_r$ is slightly lower than room temperature and its $M_d$ is not lower than room temperature, the requirements for the occurrence of superelasticity as shown in FIG. 9 are partly satisfied. Thus it is seemingly caused by partial superelasticity effect.

$M_d$, which is the highest temperature at which stress-induced martensite is formed, is generally elevated with an increase in slip critical stress. Secondly, in case wherein $A_s$ and $A_r$ are both not higher than room temperature but the slip critical stress is low, it can be also considered that the occurrence of the complete superelasticity is inhibited by irreversible permanent deformation caused by transposition. In fact, no complete superelasticity is expressed even in a Ti—Ni alloy showing an excellent superelasticity, unless a superelastic treatment for elevating the slip critical stress is carried out. Anyway, it is considered that the above-described phenomenon is caused by an increase in partial shape recovery due to unloading of the deformation stress.

Further, a tensile test was performed to examine the mechanical properties, shape memory characteristics and super elastic characteristics of Ti—Nb—Sn alloys. In the tensile test, use was made of three alloys 16Nb4Sn, 17Nb4Sn and 18Nb4Sn. There are three reasons for the employment of these three alloys. First, the austenite transformation temperatures and the martensite transformation temperatures of these alloys had been all observed. Secondly, the invention aims at providing a shape memory alloy acting around room temperature and thus an excessively high transformation temperature and an excessively low transformation temperature are both unfavorable. From this viewpoint, these three alloys have transformation temperatures sufficiently usable as indications in this study, i.e., falling within the range of about ±100° C. The third reason resides in difference in phase transformation and phase equilibrium. Namely, 16Nb4Sn has $M_f$ of 31° C. and thus is completely in the martensitic state at room temperature. Because of having $M_s$ of −23° C., 17Nb4Sn is not in the martensitic state at room temperature but it might undergo stress-induced martensite transformation at deformation. Since it has $A_s$ of 60° C., the stress-induced martensite remains after unloading. Because of having $A_s$ of −23° C., 18Nb4Sn is not in the martensite state at room temperature and stress-induced martensite transformation seemingly disappears upon unloading. Therefore, 18Nb4Sn likely shows the superelasticity effect. Thus, there are three behavior patterns depending on the relationship between transformation temperature and test temperature. All of these patterns can be observed at room temperature by using 16Nb4Sn, 17Nb4Sn and 18Nb4Sn, which brings about advantages such that the test can be easily carried out and that the obtained data can be compared with other experimental data obtained at room temperature and discussed. Illustration is made herein based on "apparent" strain obtained by a machine test.

In the tensile test, 16Nb4Sn and 17Nb4Sn underwent elastic deformation followed by yielding and thus the gradients of these alloys became once gentle and then turned into sharp again. Also, 18Nb4Sn showed a change in the gradient due to yielding.

Since 16Nb4Sn is in the complete martensitic state at room temperature, it is considered that not slip deformation but lattice invariable deformation due to the rearrangement of martensite variant arises in the range where its gradient becomes gentle due to yielding.

On the other hand, 17Nb4Sn does not undergo martensite transformation at room temperature. Therefore, the range with the gentle gradient appears likely due to the growth of the stress-induced martensite and shift of the twin crystal plane of the stress-induced martensite thus formed. To confirm the formation of the stress-induced martensite, therefore, a 17Nb4Sn specimen, on which a 5% strain had been loaded followed by unloading, was observed under an optical microscope. Since 17Nb4Sn has $M_s$ of −23° C. and $A_s$ of 60° C., the stress-induced martensite does not disappear but can be observed after unloading. When the gauge length part of the tensile specimen, on which the stress was applied, and the knob, on which no stress was applied, were examined, martensite was observed at the gauge length part (a) but not at the knob part (b). Thus, the formation of the stress-induced martensite was confirmed and it was clarified that the range with gentle gradient was obtained by the formation of the stress-induced martensite. A number of maltensitic plates containing many parallel twin crystal structures were observed in (a). These twin crystals were in the same direction in individual crystal grains. In contrast, martensitic plate twin crystals precipitated by quenching did not show such tendency. This is seemingly because the twin crystal plane had shifted in association with the stress loaded in the tensile direction.

Considering the transformation temperature, yielding of 18Nb4Sn was also caused by the formation of the stress-induced martensite.

The yield stress was determined as the intersection point of the line extended from the elastic deformation part in the stress-strain curve and the line extended from the linear part in the range with gentle gradient. As a result, it was found out that all of the three specimens showed breaking elongations of 17% or more, indicating favorable processability.

Figure 10:
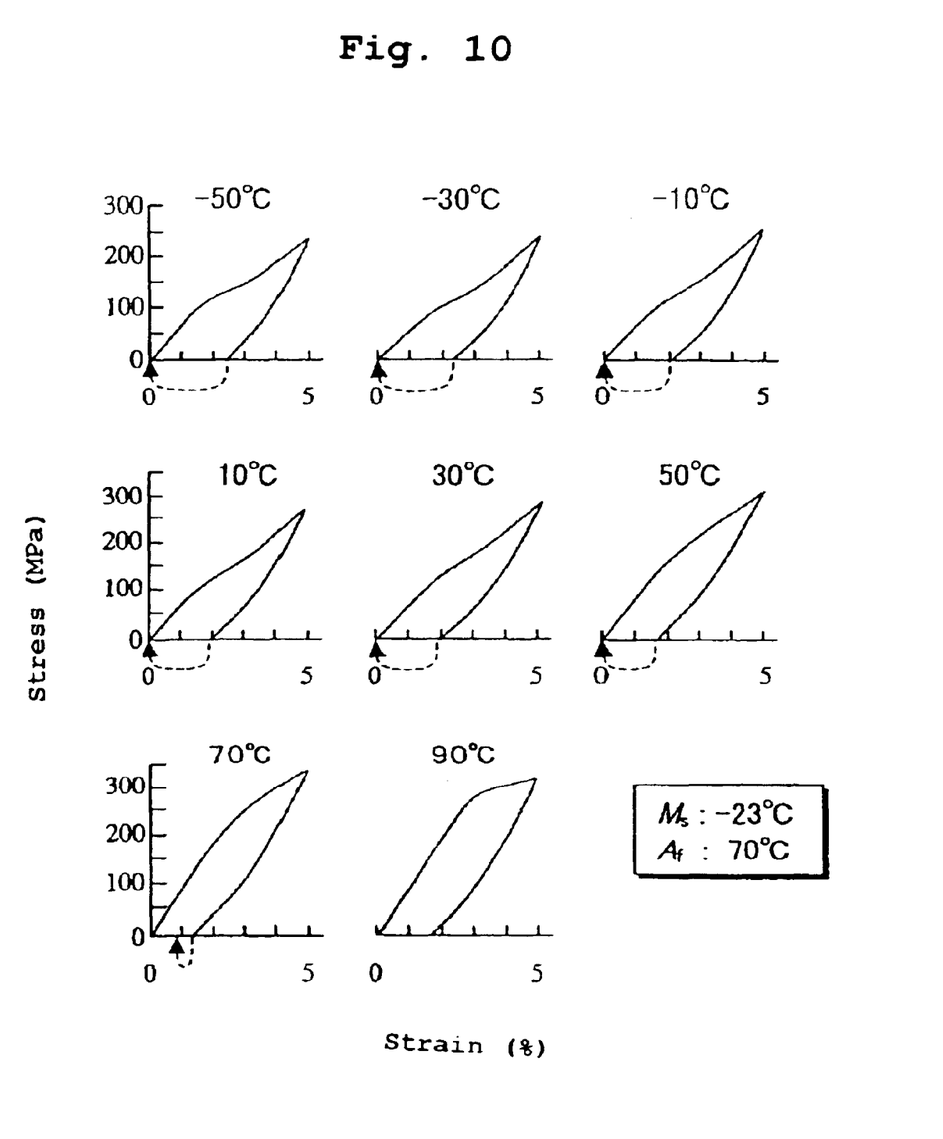
FIG. 10 shows stress-strain curves of 17Nb4Sn at various temperatures.

Based on the results of the tensile test at room temperature, another test was carried out by pulling the specimens by 4 to 5% at various temperatures (from $M_f$ or lower to $A_f$ or higher), then unloading and heating to $A_f$ or higher for recovering the shape. Since all of the three alloys tested showed similar behavior, the data of 17Nb4SN is shown in FIG. 10 as a typical case. The elastic deformation range is short in the low temperature side and yielding arises under a short stress. With an increase in temperature, the yield stress is elevated. Dotted arrows show the shape recovery after unloading and heating to A, or higher. At test temperatures of $A_f$ or lower, all of the residual strains were completely relieved by heating. On the other hand, no recovery arose at test temperatures higher than $A_f$.

As these test data clearly indicate, Nb and Ta are in the β stable phase, whereby the martensite transformation temperatures of Ti and Zr are lowered, and thus enable the achievement of the martensite transformation and shape memory effect of Ti and Zr at lower temperatures around room temperature, i.e., being applicable to human. Although Sn is an α stable type element, it can make the β phase unstable to heat and thus impart heat elasticity to martensite while causing little increase in the martensite transformation temperature. It is said that short-range order regulating the martensite reverse transformation is an important factor in the occurrence of the shape memory effect. It is expected that Sn shows a high short-range order since it has a strong interaction with Ti and Zr atoms. Therefore, Sn is advantageous in the occurrence of the stable shape memory effect from this viewpoint too. Thus, it has been clarified that shape memory characteristics can be established around 37° C. (i.e., the human bodily temperature) by adding Sn in an adequate amount so as to make the martensite transformation (i.e., shape memory characteristics) suitable for biological use.

From the above results, it is considered that the alloy of the present invention can provide a suitable shape-memory effect near the human body temperature based on the following mechanism.

Thus, the shape memory characteristics can be established around the human body temperature (i.e., 30° C. to 40° C.) by adding Sn in an adequate amount so as to make the martensite transformation (i.e., shape memory characteristics) suitable for biological use.

While the invention has been described in detail and with reference to specific examples thereof, it will be apparent to one skilled in the art that various changes and modifications can be made therein without departing from the spirit and scope thereof.

This application is based on Japanese application No. 2000-146686, the entire contents of which are incorporated hereinto by reference.

What is claimed is:

1. A Ti—Zr alloy comprising (1) Sn, (2) at least one of Ti and Zr, and (3) one of Nb and Ta;

wherein Sn is present in an amount of 3–6 at % and said alloy having shape memory and superelasticity characteristics at human body temperature.

2. The alloy as claimed in claim 1, wherein the total percentage of the Ti and Zr in said alloy is from 90 to 74 atom %.

3. The alloy as claimed in claim 1, wherein the total percentage of Nb and Ta in said alloy is from 8 to 20 atom %.

4. An orthodontic appliance comprising the alloy as defined in claim 1.

5. An artificial dental implant comprising the alloy as defined in claim 1.

6. An artificial arthrosis comprising the alloy as defined in claim 1.

7. A bone material comprising the alloy as defined in claim 1.

8. A bone fixator comprising the alloy as defined in claim 1.

9. A thrombus inhibitor comprising the alloy as defined in claim 1.

10. A catheter introducer comprising the alloy as defined in claim 1.

11. A Harrington bar comprising the alloy as defined in claim 1.

12. An artificial joint comprising the alloy as defined in claim 1.

13. An alloy comprising (1) Sn, (2) at least one of Ti and Zr, and (3) at least one of Nb and Ta;

wherein the total percentage of the Ti and Zr in said alloy is from 90 to 74 at. %, Sn is present in an amount of 3–6 at. %, and said alloy having shape memory and superelasticity characteristics at human body temperature.

14. The alloy as claimed in claim 13, wherein the total percentage of Nb and Ta in said alloy is from 8 to 20 atom %.

15. An orthodontic appliance comprising the alloy as defined in claim 13.

16. An artificial dental implant comprising the alloy as defined in claim 13.

17. An artificial arthrosis comprising the alloy as defined in claim 13.

18. A bone material comprising the alloy as defined in claim 13.

19. A bone fixator comprising the alloy as defined in claim 13.

20. A thrombus inhibitor comprising the alloy as defined in claim 13.

21. A catheter introducer comprising the alloy as defined in claim 13.

22. A Harrington bar comprising the alloy as defined in claim 13.

23. An artificial joint comprising the alloy as defined in claim 13.

* * * * *